United States Patent [19]

Frey et al.

[11] Patent Number: 4,752,295
[45] Date of Patent: Jun. 21, 1988

[54] METAL BONE IMPLANT

[75] Inventors: Otto Frey; Manfred Semlitsch, both of Winterthur, Switzerland

[73] Assignee: Sulzer Brothers Limited, Winterthur, Switzerland

[21] Appl. No.: 823,390

[22] Filed: Jan. 28, 1986

[30] Foreign Application Priority Data

Feb. 7, 1985 [CH] Switzerland ............................ 559/85

[51] Int. Cl.[4] ........................... A61F 2/28; A61F 2/32
[52] U.S. Cl. .......................................... 623/16; 623/18; 623/22; 623/23
[58] Field of Search ................. 623/23, 22, 21, 20, 623/19, 18, 17, 16; 128/92 YZ, 92 YY, 92 YX, 92 YW; 433/201.1, 202.1

[56] References Cited

U.S. PATENT DOCUMENTS

| 3,896,505 | 7/1975 | Timmermans | 623/23 |
| 4,237,875 | 12/1980 | Termanini | 128/92 YW |
| 4,287,617 | 9/1981 | Tornier | 623/23 |
| 4,608,055 | 8/1986 | Morrey et al. | 623/23 |

OTHER PUBLICATIONS

Swanson et al., *The Scientific Basis of Joint Replacement*, 1977, p. 11.

Primary Examiner—Richard J. Apley
Assistant Examiner—Alan W. Cannon
Attorney, Agent, or Firm—Kenyon & Kenyon

[57] ABSTRACT

The metal bone implant is constructed with thin sheets of superplastic material which are deformed into irregular contours. The sheets are welded to the solid base element of the implant and thereafter deformed outwardly under fluid pressure to an irregular shape.

19 Claims, 1 Drawing Sheet

METAL BONE IMPLANT

This invention relates to a metal bone implant. More particularly, this invention relates to a joint endoprosthesis having an irregular geometric shape.

As is known, in order to save weight, especially in joint endoprosthesis, such prosthesis have been made at least in part with closed cavities, such as described in French Pat. No. 6931863 (2021313). As in the case of solid prosthesis parts, the hollow parts have heretofore been made of forged and/or cast parts which are subsequently welded together in order to form a closed hollow body. One example of such a construction is described in European Patent Application No. 172262 wherein a joint head for a femur head prosthesis is formed of a hollow ball of cast material and of a sleeve of forged material which is welded to the hollow ball. However, the production and machining of these previously known prosthesis, particularly where an anchoring shank with a structure consisting of ribs is involved, has been expensive and complicated.

Bone implants have also been known, for example from European Patent Application No. 0015564 which are made of sheet metal. In these cases, the implants have been constructed as a plug-in sleeve in order to surround an anchoring shank of a minor joint, for example made of plastic. In these cases, the form of a plug-in sleeve is relatively simple so that the production of the implant generally requires no great expense and presents no difficulties. However, there is a reduction in mechanical strength of the implant as compared with those prosthesis which are formed of individual forged and cast parts.

Accordingly, it is an object of the invention to provide a metal bone implant having a hollow construction with good mechanical properties.

It is another object of the invention to provide a relatively simple technique for forming a metal bone implant with a hollow cavity.

It is another object of the invention to provide a metal bone implant of reduced weight and good mechanical properties.

Briefly, the invention provides a metal bone implant which is comprised of a metal base element and at least two sheet metal walls which are secured to the base element in order to define a hollow body of irregular geometric shape. Preferably the walls are made of a superplastic material such as alpha/beta titanium alloy and are of thin construction, for example having a thickness of at least one millimeter.

The invention also provides a method of making a hollow implant with an irregular shape and contour. The method includes the steps of securing at least one sheet metal plate on a metal base element and thereafter deforming the sheet metal plate outwardly of the base element in a mold in order to define a hollow cavity and an irregular surface thereon. Any suitable technique may be used for the final shaping of the thin sheet metal plate. Thus, even complicated exterior forms can be easily and simply made without requiring subsequent mechanical treatments.

The invention thus provides a metal bone implant which, being made of at least part hollow construction, provides a weight reduction as compared with similar solid constructions.

The walls which define the hollow portion of the implant may be such as to provide either open or closed hollow bodies. If the walls define a closed hollow body, the cavities may be filled with light weight materials of high rigidity, for example plastic foams such as polyethylene and the like or with an elastic or plastically deformable material of stable volume, such as silicone rubber or epoxy resin. Such filling serve to increase the strength and form stability of the walls.

The stability of the walls in the final form can be increased if the form is created by at least two sheets which are disposed one on the other in layer fashion. In this case, the outer sheet which should, as closely as possible, match the form and surface of the bone wall into which the implant is to be implanted may be thinner and easier to deform than the inner sheet which essentially constitutes only a support for the outer sheet.

These and other objects and advantages of the invention will become more apparent from the following detailed description taken in conjunction with the accompany drawings wherein.

Figure 1:
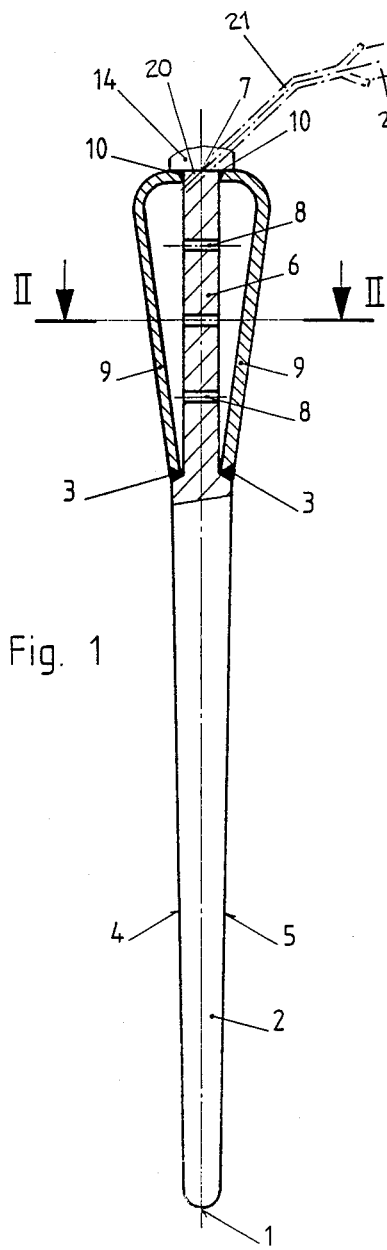
FIG. 1 illustrates a partial cross sectional view of a hip joint prosthesis constructed in accordance with the invention.

Referring to FIG. 1, the metal bone implant is in the form of a femur head prosthesis which has a straight shank 2 which flares conically from a distal end 1 towards a proximal end. As indicated, the conically flaring transverse sides 4, 5 of the shank 2 extend to a shoulder 3 and terminate in a plate-like base element 6 which extends to the proximal end 7. In addition, an enlarged prosthesis neck inception 14 is disposed at the proximal end 7 and is spatially offset against the end 7.

The base element 6 is provided with discontinuities in the form of bores 8.

In addition, the implant has a pair of sheet metal walls formed of metal sheets 9 which give form and surface to the proximal shank part. These sheets 9 also define a hollow body of irregular geometric shape within which the base element 6 is disposed. These sheets 9 may consist of a superplastic material such as an alpha/beta titanium alloy of type Ti-6Al-4v. As indicated, the lower ends of each sheet 9 are welded to the shoulder 3 of the base element while the upper ends are welded under the neck inception 14. Initially, the sheets are flat when welded to the base element 6 as indicated in FIG. 2a and are thereafter deformed into an irregular geometric shape as indicated in FIG. 2b.

Figure 2A:
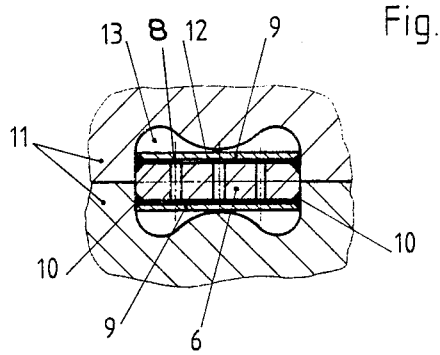
FIG. 2a illustrates an unshaped cross-section of the shank of FIG. 1 take at the level of the section II—II.

In order to make the implant, the sheets 9 are first connected in gas tight manner with the base element 6 on the entire circumference by means of the welds 1 at the shoulder 3 and weld seams 10 which extend about the remaining periphery of the sheets 9 as indicated in FIG. 2a. Next, the proximal region of the shank 2 covered by the sheets 9 is placed in a two-part hollow mold 11, the cavity of which corresponds to the negative shape of the final form of the shank 2. Thereafter a fluid pressure medium is forced via conduits and connections into a cavity 12 between the base element 6 and the sheets 9. To this end, as indicated in FIG. 1, a bore 20 which is shown schematically and marked in dash-dot line, penetrates the base element 6 from the proximal end and terminates in cavity 12 while a conduit 21 which leads from a source 22 of fluid pressure medium is connected to the bore 20 in order to deliver the fluid pressure medium. This causes an outward deformation of the sheets 9 from the base element 6 since the cavity 12 is impermeable to the pressure medium so that the sheets 9 assume the shape of the limiting walls of the mold cavity 13. After disconnecting the conduit 21, the bore 20 is closed by a plug, for example, of welding material such as the material used to form the welds at the shoulders 3 and the seams 10.

Figure 2B:
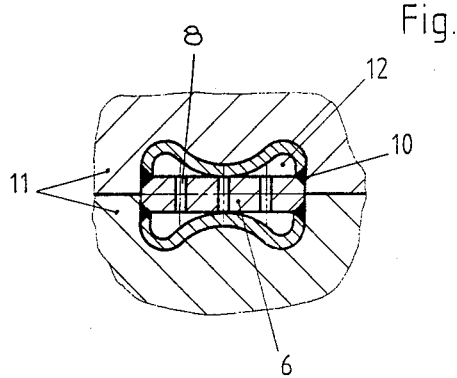
FIG. 2b illustrates a shaped cross-section of the shank of FIG. 1 at the level of section II—II.

As indicated in FIG. 2b, the bores 8 within the base element 6 permit the pressure medium to communicate with both sides of the base element 6.

Figure 3:
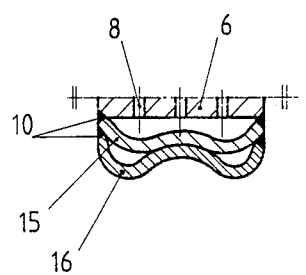
FIG. 3 illustrates a transverse section of a shank having a sheet metal wall formed of two sheets of layered construction.

Referring to FIG. 3, each wall of the implant may be formed of two sheets 15, 16 which are disposed on one another in layer fashion. In this case, the sheets are made with different deformation resistances. For example, the outer sheet 16 which is easier to deform than the inner sheet, and hence often thinner, serves to adapt the implant formed to the bone cavity. The inner sheet 15 then has the function to increase the stability of the outer sheet.

As indicated, the inner sheet 15 is welded to the base element 6 while the outer sheet 16 is welded to the inner sheet 15. In other constructions, the outer sheet 16 may completely embrace the inner sheet 15 and likewise be secured to the base element 6 directly.

The shaping of the layered sheets 15, 16 can be carried out, for example in the manner described above, and if necessary, passage openings for the pressure medium (not shown) may be present in the inner sheet 15.

The invention thus provides a metal bone implant of at least part hollow construction which has relatively good mechanical properties while providing reduced weight.

Further, the invention provides a metal bone implant wherein the outer contour of the implant can be readily shaped into an irregular contour for implantation in a bone cavity of like contour.

The use of thin sheets for the shaping of the portions of complicated form of the bone implant simplifies production and lowers the manufacturing cost noteably.

What is claimed is:

1. A biocompatible metal bone implant comprising
a biocompatible metal base element; and
at least two biocompatible sheet metal walls secured to said base element to define a hollow body of irregular geometric shape with a cavity between said base element and each respective wall.

2. A biocompatible metal bone implant as set forth in claim 1 wherein said walls are made of a superplastic material.

3. A biocompatible metal bone implant as set forth in claim 1 further comprising an elastic material of stable volume filling said hollow body.

4. A biocompatible metal bone implant as set forth in claim 1 wherein each wall includes at least a pair of sheets disposed in layered fashion.

5. A biocompatible metal bone implant as set forth in claim 4 wherein each sheet has a deformation resistance different from the other sheets.

6. A biocompatible metal bone implant as set forth in claim 1 wherein each wall has a thickness of at least one millimeter.

7. A biocompatible metal bone implant as set forth in claim 1 wherein said walls are made of as alpha/beta titanium alloy.

8. A biocompatible metal bone implant comprising
a biocompatible shank extending from a distal end to a proximal end; and
a plurality of biocompatible sheet metal walls secured to said shank to define a hollow body with said shank at said proximal end, said walls having an irregular geometric shape with at least two walls spaced from opposite sides of said shank to define a pair of cavities therewith.

9. A biocompatible metal bone implant as set forth in claim 8 wherein each wall is formed of two plates, the outer of said two plates having a lesser deformation resistance than the inner of said two plates.

10. A biocompatible metal bone implant as set forth in claim 8 wherein said walls define a closed hollow body.

11. A biocompatible metal bone implant as set forth in claim 8 wherein said walls define an open hollow body.

12. A biocompatible metal bone implant as set forth in claim 8 wherein said shank has a plate-like base element at said proximal end and each wall is secured to an opposite side of said base element.

13. A biocompatible metal bone implant as set forth in claim 12 wherein said hollow body is impermeable.

14. A biocompatible metal bone implant as set forth in claim 12 wherein each wall is peripherally welded to said base element.

15. A biocompatible metal bone implant comprising
a biocompatible anchoring shank;
a biocompatible metal base element extending from said shank; and
at least two sheet biocompatible metal walls secured to opposite sides of said base element to define a hollow body of irregular geometric shape with a cavity between said base element and each respective wall.

16. A biocompatible metal bone implant as set forth in claim 15 wherein said walls define a closed body and which further comprises an elastic material of stable volume filling said closed hollow body.

17. A biocompatible metal bone implant as set forth in claim 15 wherein each wall includes at least a pair of sheets disposed in layered fashion.

18. A biocompatible metal bone implant comprising
a biocompatible metal base element; and
at least two biocompatible sheet metal walls secured to said base element to define a hollow body of irregular geometric shape and to define an impermeable cavity with said base element.

19. A biocompatible metal bone implant comprising
a biocompatible shank extending from a distal end to a proximal end and including an enlarged neck at said proximal end and a shoulder intermediate said ends; and
a plurality of biocompatible sheet metal walls secured to said shank between said shoulder and said neck to define a hollow body with said shank at said proximal end, said walls having an irregular geometric shape.

* * * * *

UNITED STATES PATENT AND TRADEMARK OFFICE
CERTIFICATE OF CORRECTION

PATENT NO. : 4,752,295

DATED : June 21, 1988

INVENTOR(S) : OTTO FREY and MANFRED SEMLITSCH

It is certified that error appears in the above-identified patent and that said Letters Patent is hereby corrected as shown below:

Column 1, line 24 change "0015564" to -0115564-

Signed and Sealed this

Twenty-ninth Day of November, 1988

Attest:

DONALD J. QUIGG

Attesting Officer

Commissioner of Patents and Trademarks